US011426358B2

(12) United States Patent
Bracht

(10) Patent No.: US 11,426,358 B2
(45) Date of Patent: *Aug. 30, 2022

(54) MEDICAL ACTIVE SUBSTANCE PATCH WITH REDUCED OPTICAL CONSPICUOUSNESS ON THE SKIN

(71) Applicant: LTS Lohmann Therapie-Systeme AG, Andernach (DE)

(72) Inventor: Stefan Bracht, Cospeda (DE)

(73) Assignee: LTS Lohmann Therapie-Systeme AG, Andernach (DE)

( * ) Notice: Subject to any disclaimer, the term of this patent is extended or adjusted under 35 U.S.C. 154(b) by 125 days.

This patent is subject to a terminal disclaimer.

(21) Appl. No.: 16/815,286

(22) Filed: Mar. 11, 2020

(65) Prior Publication Data

US 2020/0206147 A1    Jul. 2, 2020

Related U.S. Application Data

(60) Continuation of application No. 16/265,427, filed on Feb. 1, 2019, now Pat. No. 10,646,453, which is a division of application No. 10/553,708, filed as application No. PCT/EP2004/003748 on Apr. 8, 2004, now Pat. No. 10,653,636.

(30) Foreign Application Priority Data

Apr. 17, 2003  (DE) .................. 10317692.6

(51) Int. Cl.
*A61K 9/70* (2006.01)
*A61K 31/465* (2006.01)

(52) U.S. Cl.
CPC ............ *A61K 9/703* (2013.01); *A61K 9/7023* (2013.01); *A61K 31/465* (2013.01)

(58) Field of Classification Search
None
See application file for complete search history.

(56) References Cited

U.S. PATENT DOCUMENTS

| 4,594,276 A * | 6/1986 | Relyea ................ B44C 1/105 |
| | | 428/187 |
| 5,004,610 A | 4/1991 | Osborne et al. |
| 5,120,325 A | 6/1992 | Dow, Jr. |
| 5,372,819 A | 12/1994 | Godbey et al. |
| 5,676,969 A | 10/1997 | Wick et al. |
| 6,080,421 A | 6/2000 | Steinborn et al. |
| 6,361,790 B1 | 3/2002 | Rolf et al. |
| 7,622,136 B2 | 11/2009 | Gale |
| 2003/0235608 A1 * | 12/2003 | Hansted ............... A61K 9/7084 |
| | | 424/449 |

FOREIGN PATENT DOCUMENTS

| CA | 2366859 A1 | 9/2000 |
| DE | 7529365 | 1/1976 |
| DE | 4030465 A1 | 4/1992 |
| DE | 19519593 | 8/1996 |
| DE | 19912623 A1 | 9/2000 |
| DE | 10053375 C1 | 1/2002 |
| JP | 62195073 | 8/1987 |
| JP | 7206624 | 8/1995 |
| WO | 00/37058 A1 | 6/2000 |
| WO | 01/78678 A1 | 10/2001 |
| WO | 02/34200 A2 | 5/2002 |

OTHER PUBLICATIONS

Notice of Opposition to European Patent No. 1615628 (dated Sep. 3, 2009).
Product Information, NicoDerm CQ, http://www.nicodermcq.com/NicodermCQ.How.aspx1 (May 8, 2008).
Report of Test Results, Japan Paint Inspection and Testing Association (Apr. 24, 2008).
"Clear NicoDerm CQ," Medical & Other News, www.docguide.com (Apr. 18, 2000).

* cited by examiner

*Primary Examiner* — Kevin S Orwig
(74) *Attorney, Agent, or Firm* — ProPat, LLC; Cathy R. Moore

(57) ABSTRACT

A transparent or translucent medical active substance patch is provided that includes a matrix of monolayer or multilayer configuration with at least one active substance-containing layer contained therein and a backing layer connected with the matrix. The patch, having been applied to the skin of a first person, has a lightness color value $L_1$ at a place of the skin covered by the patch which is not less than 50% and not more than 200% of a lightness color value $L_2$, with $L_2$ being the lightness value of the region of skin of the same person which surrounds the applied patch, with the same being true of the skin of a second or any other person, provided that for all the persons mentioned, the $L_2$ of their respective skin is in the range from 5° to 100°, especially in the range from 20° to 90°.

12 Claims, 1 Drawing Sheet

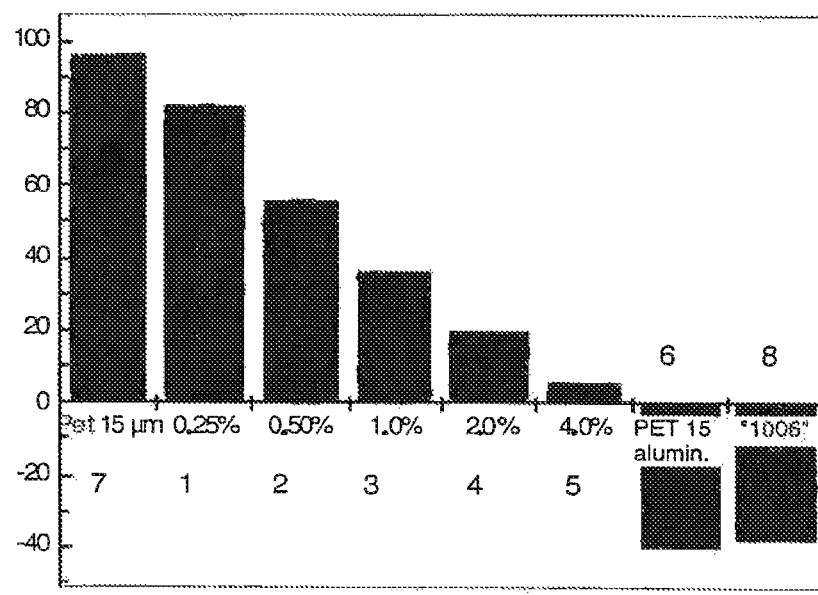

MEDICAL ACTIVE SUBSTANCE PATCH WITH REDUCED OPTICAL CONSPICUOUSNESS ON THE SKIN

CROSS-REFERENCE TO RELATED APPLICATIONS

This Continuation Application claims priority to parent application, U.S. patent application Ser. No. 16/265,427, filed Feb. 1, 2019, allowed, which claims priority to U.S. patent application Ser. No. 10/553,708, filed Jun. 16, 2006, allowed, which claims priority to PCT/EP04/03748, filed Apr. 8, 2004, and German Patent application 10317692.6, filed Apr. 17, 2003. Each of the foregoing U.S. patent application Ser. Nos. 16/265,427 and 10/553,708, PCT Application No. PCT/EP04/03748 and German Patent Application No. 10317692.6 are hereby incorporated herein by reference in their entirety.

FIELD OF THE INVENTION

The present invention relates to medical active substance patches, particularly to transdermal therapeutic systems, comprising a monolayer or multilayer, active substance-containing matrix and a backing layer connected with said matrix, said active substance patches being distinguished by an improved optical appearance when being worn on the skin.

The invention further encompasses processes enabling the production of such active substance patches.

BACKGROUND OF THE INVENTION

Many of the active substances or auxiliary agents suitable for use in the manufacture of active substance patches or TTSs show a tendency to discolor, for example to yellow. Such adverse changes may also occur during the application period. It is known, for instance, that nicotine patches gradually turn yellow.

The aforementioned changes are inmost cases due to oxidative decomposition processes which progress upon contact with atmospheric oxygen and moisture especially during storage of the active substance patch or when it is being worn on the skin and which are promoted by action of light. Particularly affected by such processes are pharmaceutical active substances, antioxidants, various enhancers (i.e. substances promoting or accelerating transdermal active substance absorption), as well as oxidation-sensitive components of the pressure-sensitive adhesive that is present in the active substance patch, such as resin adhesives, for example.

The extent of active substance decomposition does not necessarily have an adverse effect on the pharmaceutical quality of the products, for instance if the resulting decomposition products amount to only fractions of a weight percent of the starting composition and if these decomposition products are toxicologically acceptable. Thus, discoloration often already affects a product cosmetically whereas the pharmaceutical quality is still unimpaired. Frequently, users or patients especially in the case of medicaments associate such disadvantageous changes in the optical appearance of the active substance patches with defectiveness or deterioration, which causes a feeling of insecurity in those patients.

Often these changes are yellow, brown or red discolorations as typically appear in chemical decomposition. Even slight changes in color may be interpreted by the users or patients as indicative of a deterioration of the quality of the medicament.

The problem of discoloration occurs particularly if the product, in fresh condition after manufacture, initially appears colorless or white to the human eye and the above-mentioned discoloration occurs only after a certain period of storage or while the patch is being worn on the skin. This is perceived by the users to be even more critical and potentially dangerous than a discoloration which has been there from the start and only becomes more intense during storage.

In the field of medical active substance patches, transparent and colorless patches represent the ideal case in respect of cosmetics since the user himself or other persons regard them as inconspicuous when applied to the user's skin. Users of medicinal patches generally prefer patches with such inconspicuous properties because they reduce the risk of other people becoming aware of the user's need for treatment and possibly finding out about his illness.

If for reasons of cosmetics a transparent design of an active substance patch does not make sense, for example because the ingredients are colored or because of discoloration occurring during storage, it is possible to equip the patch with a non-transparent backing layer. During the application period this backing layer then prevents that the color or discoloration is optically perceived.

In the latter case, it is disadvantageous, however, that patches or TTSs equipped with a nontransparent backing layer are much more conspicuous at the site of application, that is, on the patient's skin, than transparent or colorless patches. A measure known from the state of the art and frequently applied consists in applying a skin-colored lacquer to the nontransparent backing layer. This, however, leads to a further problem since it proves extremely difficult to find a skin tone that in equal measure suits a larger number of users of different skin color tone and is cosmetically acceptable. Taking into consideration all of the skin types of the world population, it is entirely impossible to determine a unitary, opaque skin color tone that would be suitable as the color tone for a nontransparent backing layer. This problem could be solved, it is true, by producing otherwise identical active substance patches having differently colored backing layers that match the different skin color tones of the world population, but this is out of the question because of the complex manufacturing and distribution logistics, and ultimately for reasons of cost.

SUMMARY OF ADVANTAGEOUS EMBODIMENTS OF THE INVENTION

The object of the present invention was therefore to provide active substance patches which despite colorations that are already existent or occurring over time ensure an optically inconspicuous appearance of the patch especially when the patch is located at the application site. The intention here is to preferably find a uniform solution which is suitable for the most different skin color tones of the world population.

A further object of the invention was to indicate processes by means of which such active substance patches can be obtained.

These objects are achieved by means of medical active substance patches according to claim 1 and by means of processes of production noted herein, as well as by means of the embodiments described in the dependent claims.

BRIEF DESCRIPTION OF THE DRAWINGS

FIG. 1 is a bar chart indicating the visual in conspicuousness of various exemplary test patches.

DETAILED DESCRIPTION OF ADVANTAGEOUS EMBODIMENTS OF THE INVENTION

Thus, the above-mentioned disadvantages do not occur or only occur in attenuated form in the medical active substance patches described in the introductory part of the present application if the active substance patch is transparent or at least translucent and if—in the state of having been applied to a person's skin—said patch, in an area of the skin covered with the patch, has a lightness color value $L_1$ which is not less than 50% and not more than 200% of a lightness color value $L_2$, $L_2$ being the lightness value of the region of the skin of the same person which surrounds the applied patch, and if the same is true in respect of the skin of a second or any other person, provided that L,2, for all the persons mentioned, is in a range from 5° to 100°, especially in a range from 20° to 90°. The aforementioned differences between the lightness values $L_1$, $L_2$ can be determined by measurements in representative spot checks of people of the respective skin type.

The color value of the lightness L, designated as "lightness color value" is a colorimetric characteristic value which, in conjunction with other characteristics, is used in engineering for the non-ambiguous characterization of colors. The lightness color value is indicated in degrees and can be determined by color measuring instruments. The values of color lightness indicated herein were determined by means of a tristimulus colorimeter, such as Surprisingly, it emerged that active substance patches having the aforementioned features of the invention were of inconspicuous appearance at the place of application, i.e. on the skin, and that such active substance patches are optically inconspicuous on the most different skin color types of the world population. For example, an active substance patch of the invention has an equally inconspicuous optical appearance when applied to the skin of a user of Caucasian, light skin color or to the skin of a user of dark, Negroid skin color. For this reason, according to a preferred embodiment an active substance patch of the invention is characterized in that the lightness color value $L_2$ of the said first person, measured in the area of the skin not covered by the patch, is the lightness color value of a person of light, Caucasian skin color, and that the lightness color value L2 of the said second person is the lightness color value of a person of dark, negroid skin color, or vice versa.

The manufacture of active substance patches having the features of the introductory part of claim 1 and the substances suitable for said manufacture are in principle known to those skilled in the art. Substances which may be used to produce the matrix layer(s) are, for instance, from the group of the polyacrylates, poly(meth)acrylates, adhesive resins, cellulose derivatives, polyisobutylenes, styrene-isoprene-styrene block copolymers, styrene-butadiene-styrene block copolymers, polydimethyl siloxane, ethylene vinyl acetate copolymers and vinyl acetate, optionally with addition of auxiliary substances known to the skilled artisan. At least one of the matrix layers contains an active substance, the term active substance referring, in particular, to a pharmaceutical active substance or a plurality of such substances.

The active substance patches of the invention, which are comprised of a matrix and a superimposed backing layer, are substantially transparent or at least translucent (i.e. transmitting light but not transparent) and in any case not opaque. Thus, the backing layer is also substantially transparent or translucent.

Suitable as a backing layer are, first of all, polyesters, such as polyethylene terephthalate (PET) and polybutylene terephthalate, but also almost any other skin-compatible plastics, such as polyvinyl chloride, ethylene vinyl acetate, vinyl acetate, polyethylene, polypropylene, cellulose derivatives and many others.

According to a preferred embodiment, the active substance patches of the invention contain one or more substances from the group of the dyes and pigments in at least one of their layers. In combination with the transparent or translucent properties of the patch it is thereby achieved that a coloration of the matrix ingredient(s) which has been existing from the start or a discoloration of said ingredients which has begun and intensifies only after the patch has been manufactured is optically masked. At the same time, the color is thereby sufficiently adapted to the skin tone of the application site so that the patch will be inconspicuous on the most different skin color types. Preferably the substance(s) used for optical masking, which are selected from the group of the dyes and pigments, are contained in the matrix layer or in at least one of the matrix layers of a multilayer patch.

According to a further, particularly preferred embodiment, optical masking is achieved by providing the transparent or translucent backing layer with a content of at least one substance selected from the group of the dyes and pigments. This can be accomplished, in particular, by coating the backing layer of the patch on its outer side, that is, on the side averted from the skin, with a coating or a lacquer which contains at least one dye or/and at least one pigment. This variant has the additional advantage that the dye(s) or pigment(s) cannot come into contact with the active substance-containing matrix.

It may further be of advantage for both the matrix layer(s) and the backing layer to contain a dye or dyes and/or a pigment or pigments.

It has, surprisingly, emerged that it is not so much the adaptation of the dyes or pigments to the respective skin tone which is decisive, rather this effect is essentially determined by the concentration(s) of the dyes or/and pigments utilized. The optical conspicuousness of an active substance patch is substantially determined by the concentrations of the dyes and pigments contained therein. In addition, the layer thickness of the patch must be taken into consideration in this connection. In order for the patch to be inconspicuous to the eye of a beholder, certain concentrations of the dyes or/and pigments (inclusive of the colored or discolored ingredients, in particular active substances) must not be exceeded. These concentrations can be determined by means of the conditions mentioned in claim 1.

At low concentrations of the colored or discolored ingredients comprised in the matrix, even such dyes or pigments can still be optically inconspicuous as clearly deviate from the color tone of the underlying skin at the place of application. The same applies if the patch is of a small layer thickness. The low concentration and/or the small layer thickness results in a scope for the concentration or in corresponding possibilities of varying the layer thickness, thus fulfilling the requirements for optical masking of discolorations of ingredients of active substance patches by admixing dyes and/or pigments.

A further improvement of the optical appearance of active substance patches applied to the skin can be achieved, according to a particularly preferred embodiment, by providing at least that surface of the backing layer which is averted from the skin with reduced reflection properties. This can either be accomplished by means of physical methods or by applying an antireflection layer or antireflection coating. Such a layer or coating preferably contains an optical dulling agent or a combination of at least two dulling agents. This antireflection layer may at the same time contain a dye or dyes or/and a pigment or pigments to mask the ingredients of the patch, as described above.

In addition, it is possible by matting to eliminate or reduce that cause of optical conspicuousness of an active substance patch which is due to light reflection. Such light reflection frequently occurs in active substance patches which are provided with a transparent backing layer of smooth surface structure. The reflection properties of these backing layer materials differ greatly from the reflection properties of human skin, which is why such plasters are visually very conspicuous on the skin.

The active substance patches of the present invention are particularly advantageous if at least one layer of the matrix comprises one or more colored ingredient(s). This may, in particular, be a substance or substances which is/are colorless in its/their initial state and which has/have a tendency to discolor or which discolor during storage or during the application period. Particularly preferred are active substance patches which contain one or more pharmaceutically active substances as colored ingredients or as ingredients which have a tendency to discolor, with particular preference for nicotine.

Preferably, the active substance patches mentioned are transdermal therapeutic systems. These are distinguished by enabling a constant delivery of active substances via the skin for a determined period of time. The structure and manufacture of such systems are in principle known to those skilled in the art.

The invention further encompasses processes for the production of the above-described active substance patches. These processes comprise the following steps:
(a) producing a system comprising a mono- or multilayer active substance-containing matrix and a backing layer connected therewith, wherein the matrix is produced by using (a) matrix polymer(s), (an) active substance(s) and auxiliary agents, and wherein one or more substance(s) selected from the group of the dyes and pigments is/are admixed to the matrix or/and the backing layer;
(b) producing at least one further system according to step (a), this system being different in terms of the concentration of the dyes or/and pigments, and/or in terms of the type of the dyes or/and pigments used;
(c) producing surface sections or punched pieces from the systems obtained in steps (a) and (b);
(d) producing or providing color charts with lightness color values $L_2$ in the range from 5° to 100°, particularly in the range from 20° to 90°,
(e) applying or affixing the sections or systems obtained in step (c) to the color charts mentioned in (d);
(f) measuring the color values of the lightness $L_1$ of the systems located on the color charts and determining the difference between $L_2$ and $L_1$ in each particular case;
(g) selecting those systems with a color value of the lightness $L_1$ which is not less than 50% and not more than 200% of the lightness color value $L_2$.

Through the teaching of the present invention it is made possible to produce active substance patches which despite containing colored or discoloring ingredients are not easily perceivable to an observer and are optically inconspicuous when being worn on the skin, independently of whether the patch is attached to the skin of a light-skinned or dark-skinned person.

The invention will be illustrated in greater detail by means of the following examples.

EXAMPLES

1. Preparation of Backing Layers of Different Pigment Concentrations

Coating compounds were prepared from ethyl cellulose and different portions of a pigment mixture (see Table 1) and these compounds were coated by means of a doctor knife to a PET film of 15 μm thickness (weight per unit area 7-10 g/m²).

TABLE 1

| No. | Ethyl cellulose [%-wt.] | Pigment mixture [%-wt.] |
|---|---|---|
| 1 | 99.75 | 0.25 |
| 2 | 99.5 | 0.5 |
| 3 | 99.0 | 1.0 |
| 4 | 98.0 | 2.0 |
| 5 | 96.0 | 4.0 |

Pigment Mixture:
  50.0%-wt. of NATURELL® BB Ply Pigment
  50.0%-wt. of NATURELL® Pulver Pigment
  (from Cosnaderm Chemische Rohstoffe GmbH, D-68526 Ladenburg)

Used as Control Examples were:
  (6) PET film, aluminized and nicotine-resistant (nontranslucent)
  (7) PET film, 15 μm, transparent
  (8) SCOTCHPAK® 1006

2. Preparation of Skin Patches

Skin patches were produced using the backing layers prepared under "1" above. To this end, DUROTAK® 2052 (National Starch &. Chemical B.V.) was spread at a weight per unit area of 80 g/m² and in each case covered with one of the backing layers mentioned under "1" above in Table 1. Subsequently, individual patches, each patch of a size of 1 cm², were punched out.

3. Preparing Color Charts Corresponding to the Human Skin Colors

By means of the software "PowerPoint" (Microsoft) and a color printer (HP-C LASERJET® 4500; Hewlett-Packard) eight color charts were established representing the various skin color tones of the world population.

The color tones of the color charts are characterized in "PowerPoint" by the six parameters: color tone, red, green, blue, saturation, intensity as listed in Table 2 below, and can be re-produced by means of these parameters:

TABLE 2

| Color chart No. | Color tone | Red | Green | Blue | Saturation | Intensity |
|---|---|---|---|---|---|---|
| A | 16 | 255 | 215 | 191 | 255 | 223 |
| B | 21 | 50 | 25 | 0 | 255 | 25 |
| C | 21 | 80 | 40 | 0 | 255 | 40 |
| D | 21 | 255 | 236 | 217 | 255 | 236 |
| E | 21 | 197 | 137 | 77 | 130 | 137 |
| F | 21 | 72 | 36 | 0 | 255 | 36 |
| G | 21 | 117 | 78 | 39 | 128 | 78 |
| H | 25 | 255 | 226 | 183 | 255 | 219 |

The color charts Nos. A-H were measured using a tristimulus colorimeter, CP-320, from Techkon GmbH (DE-61462 Konigstein). The values (in degrees) for the lightness L, the red-green axis a, and the yellow-blue axis b were determined. For each color chart, 10 measurements were made and the mean values determined. The mean values are represented in the following Table 3.

TABLE 3

| Color chart No. | L Value ($L_2$) | a Value | b Value |
|---|---|---|---|
| A | 82.464 | 10.986 | 13.634 |
| B | 21.791 | −3.203 | 8.877 |
| C | 25.776 | 5.905 | 14.758 |
| D | 88.086 | 4.945 | 9.572 |
| E | 50.596 | 10.893 | 36.304 |
| F | 25.811 | 3.747 | 12.968 |
| G | 32.562 | 5.519 | 21.015 |
| H | 83.228 | 6.712 | 24.95 |
| Mean value* | 51.289 | 5.688 | 17.758 |

*These are the respective mean values determined using the values of the 8 color charts.

As can be seen, the color value of the lightness, L, varies most, whereas the "a" value differs only slightly.

The range of the skin colors for which the principle of the present invention can be advantageously employed, according to the above-described "L, a, B" system particularly comprises the range of "5,8,60" up to "100,4,0".

4. Determining the Differences in Lightness Value

The punched skin patches described under "2" above were adhered to the color charts described under "3" above. Subsequently, the lightness color values $L_1$ of the affixed patches were determined using the measuring method described under 3. From the measurement values $L_1$ obtained, the difference to the lightness value $L_2$ of the respective background (i.e. the color chart) was determined in each case. The percentage differences between the lightness color values $L_1$ of the patch types (Nos. 1 to 5 and controls Nos. 6 to 8) affixed to the color charts A to H on the one hand and the lightness values $L_2$ of the respective color charts A to H on the other hand are represented in Table 4.

It is evident therefrom that on all the color charts the transparent PET film (7) shows the smallest deviations in respect of the lightness value (positive control).

Conversely, the largest deviations were found in the control examples (6) and (8).

5. Visual Evaluation

Since it is known that the color perception of humans can deviate from the colorimetrically determined data, a visual assessment of the test patches affixed to the color charts A to H, inclusive of the comparison examples 6 to 8, was carried out by test subjects.

To this end, a certain number (e.g. 10) of each of the test patches (1 to 8) was affixed to the color charts A to H. These color charts were presented to a group of test subjects under standardized conditions (lighting, distance, time for observing). The number of the patches that were not detected by the probands was used—after statistical evaluation of the data—as a measure for the optical inconspicuousness and thereby the effectiveness of the optical masking of a patch.

In FIG. 1 the individual test patches Nos. 1-8 are represented in the form of a bar chart in the order of their visual inconspicuousness (vertical axis). Patch No. 1 and control Patch No. 7 were not perceivable or hardly perceivable on most of the color charts.

TABLE 4

| | 15 µm trsp. (No. 7) |
|---|---|
| | L |
| A | 2.733 |
| B | 13.735 |
| C | 3.236 |
| D | 5.244 |
| E | 1.435 |
| F | 12.254 |
| G | 1.388 |
| H | 5.022 |

| | nontransparent PET film 15 µm, alum. |
|---|---|
| | L |
| A | 1.42 |
| B | 273 |
| C | 215 |
| D | 7.89 |
| E | 60.3 |
| F | 215 |
| G | 150 |
| H | 2.65 |

| | SCOTCHPAK ® 1006 (No. 8) |
|---|---|
| | L |
| A | 2.903 |
| B | 267.078 |
| C | 210.289 |
| D | 9.157 |
| E | 58.254 |
| F | 209.79 |
| G | 144.61 |
| H | 4.059 |

| | 0.25% Pigment (No. 1) |
|---|---|
| | L |
| A | 6.5 |
| B | 25.5 |
| C | 12.6 |
| D | 8.13 |
| E | 6.35 |
| F | 17.8 |
| G | 7.07 |
| H | 7.51 |

| | 0.50% Pigment (No. 2) |
|---|---|
| | L |
| A | 6.978 |
| B | 22.133 |
| C | 7.294 |
| D | 5.325 |
| E | 4.577 |
| F | 17.144 |
| G | 4.53 |
| H | 3.189 |

TABLE 4-continued

| 1.00% Pigment (No. 3) | |
|---|---|
| | L |
| A | 9.94 |
| B | 7.81 |
| C | 1.51 |
| D | 10.6 |
| E | 6.4 |
| F | 10.8 |
| G | 3.19 |
| H | 10.2 |

| 2.00% Pigment (No. 4) | |
|---|---|
| | L |
| A | 14.387 |
| B | 1.647 |
| C | 4.058 |
| D | 8.295 |
| E | 33.528 |
| F | 1.794 |
| G | 2.709 |
| H | 13.731 |

| 4.00% Pigment (No. 5) | |
|---|---|
| | L |
| A | 9.29 |
| B | 54.5 |
| C | 19.2 |
| D | 21.6 |
| E | 4.53 |
| F | 28.4 |
| G | 17.9 |
| H | 20 |

That which is claimed:

1. A medical active substance patch comprising a mono layer or multilayer matrix and a backing layer connected with said matrix, said backing layer having one side averted from the skin, at least one layer of the matrix contains a pharmaceutically active substance, and at least one layer of the matrix contains an ingredient selected from the group consisting of at least one colored ingredient and at least one colorless ingredient being colorless in an initial state and tending to discolor or to discolor(s) during storage or to discolor during the application period; said at least one colored ingredient and said at least one colorless ingredient are selected from the group consisting of a pharmaceutically active substance and an auxiliary agent;

said active substance patch comprises at least one pigment admixed into a coating on the backing layer to impart a lightness color value $L_1$ that renders the patch optically inconspicuous on a person's skin;

wherein said patch has a lightness color value $L_1$ which is not less than 50% and not more than 200% or a lightness color value $L_2$, with $L_2$ being the lightness value of the region of the skin of the same person which surrounds the applied patch, and the pigments admixed into the coating on the backing layer range in an amount of from 0.25 to 0.5 wt % and deviate from the color tone of the skin underlying the patch, with the lightness color values $L_1$ and $L_2$ determined via a tristimulus colorimeter;

said patch optically masks discoloration due to decomposition promoted by light that begins and intensifies after the patch has been manufactured; said patch comprises at least one substance selected from the group consisting of skin tone dyes and pigments;

said patch is transparent or transtucent;

a surface of the backing layer which is averted from the skin has been provided with reduced reflection properties; and the reduced reflection properties are imparted by either physical iriethods or by applying an antireflection. layer or antireflection coating.

2. The medical active substance patch according to claim 1, wherein said antireflection layer or antireflection coating contains at least one optical dulling agent.

3. The medical active substance patch as claimed in claim 1, wherein said patch comprises an antireflection layer and said antireflection layer further contains one or more of at least one dye or at least one pigment that masks the ingredient(s) of the patch.

4. The medical active substance patch according to claim 1, wherein the reduced reflection properties are imparted by physical methods.

5. The medical active substance patch as claimed in claim 1, wherein the backing layer is transparent and the reduced reflection properties are imparted by matting.

6. The medical active substance patch according to claim 1, wherein said active substance patch contains said at least one substance selected from the group consisting of skin tone dyes and pigments in the matrix layer or in at least one of the matrix layers.

7. The medical active substance patch according to claim 1, wherein said ingredient which is colorless in its initial state and which has a tendency to discolor or which diseolor(s) during storage or during the application period is a pharmaceutical active substance.

8. The medical active substance patch according to claim 1, wherein said pharmaceutical active substance is nicotine.

9. The medical active substance patch according to claim 1, wherein said active substance patch is a transdermal therapeutic system.

10. The medical active substance patch according to claims 1, wherein $L_2$ is in the range from 20° to 90°.

11. The medical active substance patch according to claim 1, wherein. said skin has numerical values according to the "L, a, b" system, said numerical values ranging from "5, 8, 60" to "100, 4, 0" in said "L, a, b" system.

12. The medical active substance patch according to claim 1, wherein said patch is transparent.

* * * * *